(12) United States Patent
Miyake et al.

(10) Patent No.: US 7,306,335 B2
(45) Date of Patent: Dec. 11, 2007

(54) VISUAL TRAINING METHOD AND VISUAL TRAINING DEVICE

(75) Inventors: Nobuyuki Miyake, Hiratuka (JP); Masaki Ootsuki, Yokohama (JP); Tsuneto Iwasaki, Kitakyushu (JP)

(73) Assignee: Nikon Corporation, Tokyo (JP)

( * ) Notice: Subject to any disclaimer, the term of this patent is extended or adjusted under 35 U.S.C. 154(b) by 678 days.

(21) Appl. No.: 10/809,412

(22) Filed: Mar. 26, 2004

(65) Prior Publication Data

US 2004/0257528 A1    Dec. 23, 2004

(30) Foreign Application Priority Data

Mar. 28, 2003 (JP) ............... 2003-092014

(51) Int. Cl.
*A61B 3/00* (2006.01)
*A61B 3/02* (2006.01)
*A61B 3/08* (2006.01)
*A61B 3/10* (2006.01)

(52) U.S. Cl. .............. 351/203; 351/202; 351/205; 351/211; 351/232

(58) Field of Classification Search ........ 351/200–203, 351/205, 209, 211, 222, 232, 233, 239, 246; 434/19, 32, 33, 43, 44; 606/204.25; 600/558
See application file for complete search history.

(56) References Cited

U.S. PATENT DOCUMENTS

| | | | |
|---|---|---|---|
| 2,184,131 A * | 12/1939 | Taylor | .............. 351/232 |
| 2,213,467 A | 9/1940 | Greenspoon | ............... 351/203 |
| 2,294,408 A * | 9/1942 | Karnes | ................ 434/19 |
| 2,473,651 A | 6/1949 | Katz | ................ 351/203 |
| 2,711,594 A * | 6/1955 | Hickey | ................ 434/32 |
| 2,938,279 A * | 5/1960 | Hemstreet et al. | ........... 434/44 |
| 3,460,530 A * | 8/1969 | Lorenz | ................ 606/204.25 |
| 3,875,934 A | 4/1975 | Sadanaga | ............... 351/203 |
| 6,364,485 B1 | 4/2002 | Fatch | ................ 351/203 |

FOREIGN PATENT DOCUMENTS

| | | |
|---|---|---|
| GB | 346235 | 4/1931 |
| GB | 388200 | 2/1933 |
| GB | 459761 | 1/1937 |
| GB | 711326 | 6/1954 |
| JP | A 6-339501 | 12/1994 |
| JP | A 8-243137 | 9/1996 |
| JP | A 10-282449 | 10/1998 |

* cited by examiner

*Primary Examiner*—Loha Ben
(74) *Attorney, Agent, or Firm*—Oliff & Berridge PLC

(57) ABSTRACT

In a visual training device and a visual training method, different targets are displayed for right and left eyes, respectively, and refractivities of the right and left eyes are measured. Based on the measured refractivities of the eyes, positions of the targets displayed for the right and left eyes are moved in the directions of the respective optical axes. At the same time, the targets are moved so that the visual axes of the right and left eyes incline outward toward the end. The directions of the visual axes of the right and left eyes incline outward toward the end, so that it is possible to relax the strain of musculus ciliaris and relieve visual fatigue through short, effective training.

17 Claims, 7 Drawing Sheets

FIG. 6

|  | NORMAL(A) | AFTER TRAINING(B) | B−A |
|---|---|---|---|
| sub. 1 | 1.22 | 1.54 | 0.32 |
| sub. 2 | 0.9 | 1.06 | 0.16 |
| sub. 3 | 1.38 | 1.14 | −0.24 |
| sub. 4 | 1.06 | 1.3 | 0.24 |
| sub. 5 | 0.98 | 1.14 | 0.16 |
| sub. 6 | 0.74 | 0.9 | 0.16 |
| sub. 7 | 1.14 | 1.06 | −0.08 |
| sub. 8 | 0.9 | 0.98 | 0.08 |
| sub. 9 | 1.06 | 0.9 | −0.16 |
| sub. 10 | 1.14 | 1.22 | 0.08 |
| sub. 11 | 1.14 | 1.38 | 0.24 |
| sub. 12 | 0.82 | 0.9 | 0.08 |
| AVERAGE | 1.04 | 1.126666667 | 0.086666667 |
| STANDARD DEVIATION | 0.180906807 | 0.204198359 | |

FIG. 7

|  | NORMAL(A) | AFTER TRAINING(B) | B−A |
|---|---|---|---|
| sub. 1 | 1.17 | 1.06 | −0.11 |
| sub. 2 | 0.98 | 1.26 | 0.28 |
| sub. 3 | 1.3 | 1.3 | 0 |
| sub. 4 | 0.98 | 0.66 | −0.32 |
| sub. 5 | 1.06 | 0.9 | −0.16 |
| sub. 6 | 0.82 | 0.9 | 0.08 |
| sub. 7 | 1.14 | 1.3 | 0.16 |
| sub. 8 | 1.06 | 0.98 | −0.08 |
| sub. 9 | 1.14 | 1.14 | 0 |
| sub. 10 | 1.06 | 1.06 | 0 |
| sub. 11 | 1.06 | 1.14 | 0.08 |
| sub. 12 | 0.82 | 0.82 | 0 |
| AVERAGE | 1.049166667 | 1.043333333 | −0.00583333 |
| STANDARD DEVIATION | 0.137870712 | 0.199969695 | |

VISUAL TRAINING METHOD AND VISUAL TRAINING DEVICE

CROSS REFERENCE TO RELATED APPLICATION

This application is based upon and claims the benefit of priority from Japanese Patent Application No. 2003-092014, filed on Mar. 28, 2003, the entire contents of which are incorporated herein by reference.

BACKGROUND OF THE INVENTION

1. Field of the Invention

The present invention relates to a method and a device for visual training which are suitable for easing eyestrain of a trainee by displaying targets to his or her eyes and moving the targets in optical axis directions as well as in a convergent direction or a divergent direction (in a horizontal direction of both eyes).

2. Description of the Related Art

In this age of information society, our eyes are often overworked through visual works at near distances such as works on the screens of a television, a personal computer, and the like.

Normally, our eyes see various objects at various distances so that the musculus ciliaris of the eyes repeat relaxation and contraction for appropriate accommodation. However, excessive near-distance works on the screen of a personal computer or the like and keep viewing an object at a same distance cause the eyes not to perform accommodation. As a result, the musculus ciliaris are kept strained for a long time. The long period of strain causes the musculus ciliaris to suffer from fatigue which leads to strain of an eye accommodation system to result in decreased vision. It is said that accommodative spasm occurs if the strained state of the musculus ciliaris further persists. This brings about troubles in visibility and various kinds of stresses.

There have been proposed devices for easing eyestrain by relaxing the tension of the musculus ciliaris of the eye through training so as to eliminate fatigue.

A first example of the proposed devices is simply structured to move a target for the eyes of a trainee from near to far. The trainee's keeping watching the target, following the movement of the target from a close position to a distant position can allow the musculus ciliaris to change from a strained state to a relaxed state. In other words, the movements of the target help the musculus ciliaris be trained. (disclosed in Japanese Unexamined Patent Application Publication No. 6-339501).

However, such a device is disadvantageously large in size to be installed in households or hospitals because the target serving as a tracked object is moved from a very close position to the eyeball of the trainee such as 20 cm from the eye to a far position, for example, about 2 m from the eye.

A second proposed optical device is an optical device which uses an optical lens to reduce a distance of a moving target for the purpose of reducing the size of the device. This device achieves an effect equivalent to that of the first device in which the trainee keeps watching the moving target over a long distance from a position immediately before the eye. Furthermore, this optical device can change a distance in an optical axis direction while moving the target in accordance with a horizontal change of the eyes of the trainee (referred to as convergence or divergence), realizing a situation close to a real working situation of the eyes. (disclosed in Japanese Unexamined Patent Application Publication No. Hei 10-282449).

Herein, the above-mentioned horizontal change of the eyes is explained. As shown in FIG. 8, when a person sees an object with his or her eyes at different distances, the visual axes of both eyes are nearly parallel to each other at seeing from a long distance. On the other hand, at seeing from a shot distance, the visual axes of the eyes goes inward from the parallel state. This is generally called as convergence (represented by a convergence angle θ in FIG. 8). It is apparent that the shorter the distance, the larger the convergence angle θ.

In FIG. 8, the following relation $$\tan \theta = P/2L \quad (1)$$

is established where P is a distance between both eyes, and L is a distance to a target object.

Herein, the power of a lens is generally expressed in a unit of a diopter Dp, and has the following relation:

$$Dp = 1/L \quad (2).$$

In the second device described above, the visual axes of the eyes are never out of a parallel state by convergence; that is, the visual axes of the eyes never incline outward toward the end.

In the above-described first and second devises of prior art, the target is repeatedly moved, and the same repetitive movements over a certain period of time are necessary, which bores the trainee to view the target and quit the training in some cases. Therefore, these devices are disadvantageous in that it is difficult to continue the training for a long period of time.

These prior art devices have another problem that training of a short period of time is not enough to ease strained musculus ciliaris of the eyes and eliminate fatigue.

SUMMARY OF THE INVENTION

It is an object of the invention to provide a visual training method and a visual training device which are useful in medical therapies such as ease of the strained musculus ciliaris of the eyes through a short effective training so as to eliminate fatigue, activation of the accommodation system of the eyes, and prevention of excessive correction of refractivity caused by the strain of the accommodation system.

In order to achieve the above object, a visual training method according to a first aspect of the invention includes: a fist step of displaying separate targets for right and left eyes of a trainee, respectively; and a second step of moving positions of the separate targets displayed for the right and left eyes in directions of respective optical axes of the right and left eyes while simultaneously moving the positions of the separate targets in horizontal directions perpendicular to the optical axes of the right and left eyes until visual lines of the right and left eyes incline outward toward the end.

By the visual training method according to the first aspect of the invention, it is possible to relax the strain of the eyes in a short period of time since the eyes are horizontally moved until the visual lines of the eyes incline outward toward the end.

In order to achieve the above object, in the visual training method according to a second aspect of the invention it is preferable that the positions of the targets are moved further beyond far points in the optical axis directions while the positions of the targets are aligned with the focal points of the right and left eyes.

In order to achieve the above object, in the visual training method according to a third aspect of the invention it is preferable that the targets are moved in the optical axis directions and in the horizontal directions perpendicular to the optical axes in parallel until they reach predefined positions in the optical axis directions, and then the targets are moved only in the horizontal directions perpendicular to the optical axes.

In order to achieve the above object, in the visual training method according to a fourth aspect of the invention it is preferable that the positions in which the visual lines of the right and left eyes incline outward toward the end are in the proximity of the far points on the optical axes in any one of the first to third aspects of the invention. Herein, the proximity of the far point is within the range of −0.25 to +0.25 Dp from the far point as a center.

In order to achieve the above object, in the visual training method according to a fifth aspect of the invention the predefined positions in the optical axis direction in the third aspect are preferably in the proximity of a position +0.25 Dp further from the far point.

Herein, the proximity of a position +0.25 Dp further from the far point is preferably within the range of +0.15 to +0.35 Dp further from the far point although it varies depending on a state of the eyes of the trainee. However, it will never be before the proximity of the far point on the optical axis (side of the eyes of the trainee) recited in the fourth aspect.

In order to achieve the above object, the visual training method according to a sixth aspect of the invention is characterized in that the visual lines of the right and left eyes are preferably parallel to each other at the predefined positions in the optical axis directions in any one of the third to fifth aspects.

In order to achieve the above object, a visual training method according to a seventh aspect of the invention includes: a first step of displaying separate targets for right and left eyes of a trainee, respectively; a second step of moving positions of the separate targets displayed for the right and left eyes in directions of respective optical axes of the right and left eyes while simultaneously moving the positions of the separate targets in horizontal directions perpendicular to the optical axes of the right and left eyes until the visual lines of the right and left eyes incline outward toward the end; a third step of measuring refractivities of the right and left eyes; a fourth step of determining positions to which the separate targets are moved in the optical axis directions, according to results of the measurement in the third step; and a fifth step of returning to the second step to move the separate targets to the positions determined in the fourth step, and thereafter executing the third and fourth steps again.

According to the seventh aspect of the invention, it is possible to move the positions of the target in the optical axis directions in accordance with a state (refractivity) of the eyes of the trainee.

In order to achieve the above object, a visual training device according to an eight aspect of the invention includes: a target display section for displaying separate targets for right and left eyes of a trainee, respectively; an optical axial movement section for moving positions of the separate targets displayed for the right and left eyes in directions of respective optical axes of the right and left eyes; and a horizontal movement section for moving the separate targets in horizontal directions perpendicular to the optical axes of the right and left eyes until the visual lines of the right and left eyes incline outward toward the end.

In order to achieve the above object, a visual training device according to a ninth aspect of the invention includes: a target display section for displaying separate targets for right and left eyes of a trainee, respectively; a refractivity measuring section for measuring refractivities of the right and left eyes; an optical axial movement section for moving positions of the separate targets displayed for the right and left eyes in directions of respective optical axes of the right and left eyes, according to the refractivities of the right and left eyes measured by the refractivity measuring section; and a horizontal movement section for moving the separate targets in horizontal directions perpendicular to the optical axes of the right and left eyes until the visual lines of the right and left eyes incline outward toward the end, according to the refractivities of the right and left eyes measured by the refractivity measuring section.

According to the eighth and ninth aspects, it is possible to ease strain of the eyes in a short period of time because the eyes are horizontally moved until the visual lines of the eyes inline outward toward the end.

In order to achieve the above object, the visual training device according to a tenth aspect of the invention has the target display section of the eighth or ninth aspect of the invention which is preferably means for projecting an image serving as the target.

The visual training device according to an eleventh aspect of the invention preferably further includes a display section for simultaneously displaying a positional change of the target caused by the horizontal movement section and the refractivities of the eyes of the trainee measured by the refractivity measuring section.

The display section according to the eleventh aspect of the invention is able to display continuous measurement results thereon in accordance with the movements of the targets. As a result, it is possible to easily check up the training results of the trainee by simply viewing the display section.

In order to achieve the above object, a visual training method according to a twelfth aspect of the invention includes: a first step of displaying separate targets for right and left eyes of a trainee, respectively; and a second step of moving the separate targets displayed for the right and left eyes in horizontal directions perpendicular to the optical axes of the right and left eyes until the visual lines of both eyes incline outward toward the end.

According to the visual training method according to the twelfth aspect of the invention, it is possible to ease strain of the eyes in a short period of time since the eyes are horizontally moved until the visual lines of the eyes incline outward toward the end.

As described above, the present invention can provide a visual training method and a visual training device which can relax the strain of musculus ciliaris of the eyes through a short, effective training to relieve fatigue.

BRIEF DESCRIPTION OF THE DRAWINGS

The nature, principle, and utility of the invention will become more apparent from the following detailed description when read in conjunction with the accompanying drawings in which like parts are designated by identical reference numbers, in which:

FIG. 6 shows the results of training the eyes in a conventional method in which targets are repeatedly moved from near to far in the optical axes directions of the right and left eyes;

FIG. 7 shows the results of training eyes by moving targets from near to far in the directions of optical axes of the right and left eyes while moving the targets such that the parallel optical axes of the right and left eyes incline outward toward the end.

DESCRIPTION OF THE PREFERRED EMBODIMENT

Hereinafter, a preferred embodiment of the present invention will be described in detail with reference to the accompanying drawings.

Figure 1:
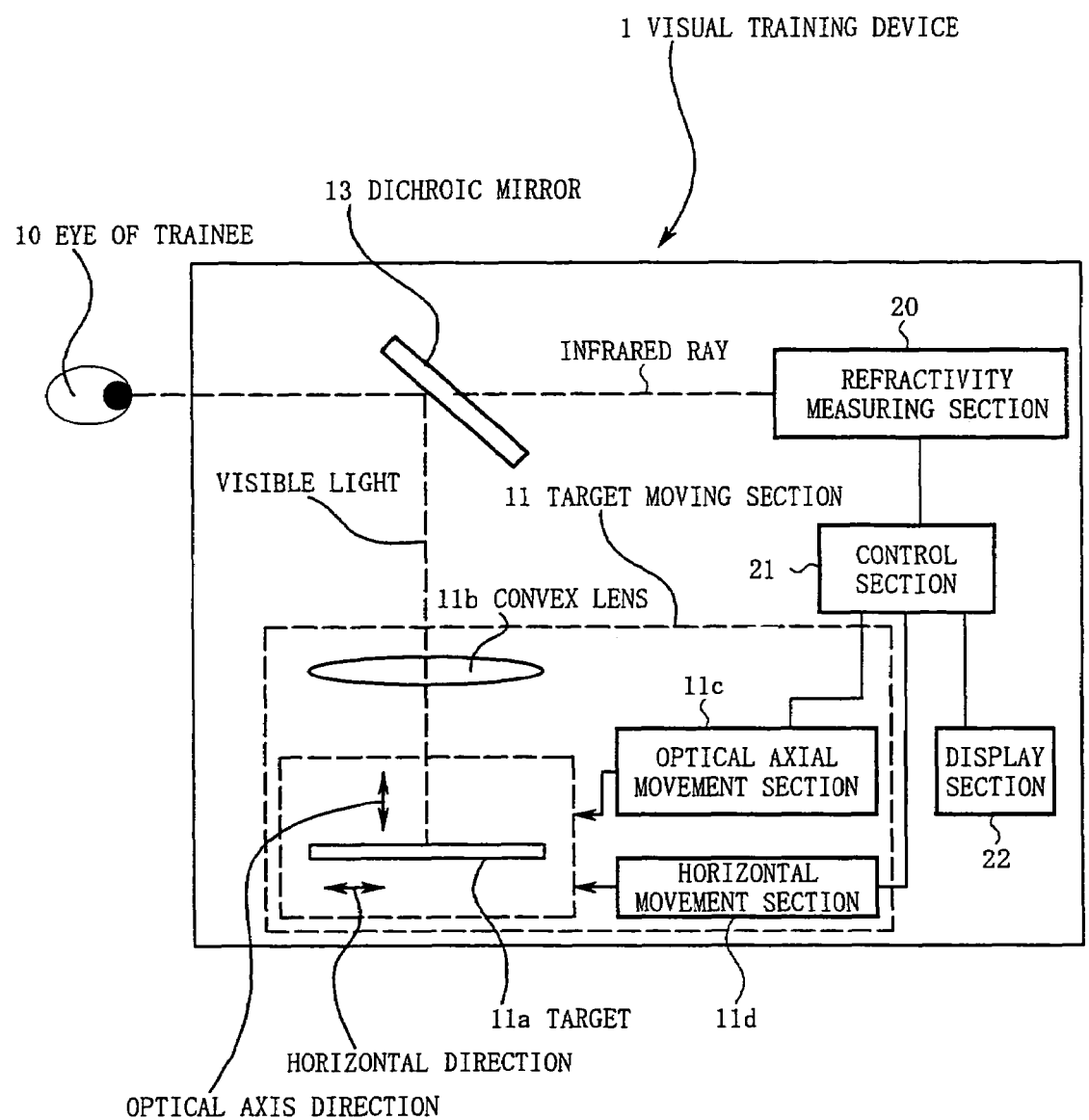
FIG. 1 is a configuration view of a visual training device showing an embodiment of the present invention.

FIG. 1 is a view showing the configuration of a visual training device according to an embodiment of the present invention. As shown in FIG. 1, a visual training device 1 includes: a target moving section 11; a dichroic mirror 13; a refractivity measuring section 20; a control section 21; and a display section 22. The target moving section 11 includes: a target 11a; a convex lens 11b; an optical axial movement section 11c; and a horizontal movement section 11d.

As shown in FIG. 1, after flux of light from the target 11a is transformed by the convex lens 11b into nearly parallel flux of light and reflected by the dichroic mirror 13, the flux of light is incident on the eye of a trainee 10. Therefore, the target 11a appears to be positioned further than it really is to the eyes of the trainee 10.

Although not shown, a pair of target moving sections 11 are provided for the right and left eyes, respectively. Therefore, the trainee views respective different targets with his right and left eyes.

The target 11a is movable in the optical axis direction as illustrated, by the optical axial movement section 11c. The target 11a is also movable in the direction horizontal with respect to the eyes of the trainee 10 as illustrated, by the horizontal movement section 11d.

The refractivity measuring section 20 constantly measures the refractivity of each eye of the trainee 10. Herein, the refractivity of the eyes of the trainee 10 is measured with an infrared ray from the dichroic mirror 13. More specifically, the eyes of the trainee 10 view only the target 11a because the dichroic mirror 13 is present. Therefore, the refractivity measuring section 20 can measure the refractivity of the trainee at any time without letting the trainee notice that his or her eyesight is being examined. The refractivity measuring section 20 outputs the measured refractivity of the eye of the trainee 10 to the control section 21.

The control section 21 is configured of a CPU, a circuit including a memory used for the operations of the CPU, and the like, and controls the driving of the optical axial movement section 11c and the horizontal movement section 11d. More specifically, the control section 21 controls the driving of motors (not shown) in the optical axial movement section 11c and the horizontal movement section 11d based on the refractivity of the eye of the trainee 10, which is output from the refractivity measuring section 20, thereby controlling the movement of an initial position (in the vicinity of a far point of the eye of the trainee 10) of the target 11a in the optical axis direction and the horizontal direction. Note that in this embodiment the refractivity measuring section 20 measures refractivity in units of diopter (Dp=1/(focal length)).

Next, the relation between the present embodiment and the appended claims will be described. A target display section recited in the claims corresponds to the target moving section 11 and the dichroic mirror 13. An optical axial movement section recited in the claims corresponds to the control section 21 and the optical axial movement section 11c. A horizontal movement section recited in the claims corresponds to the control section 21 and the horizontal movement section 11d. A refractivity measuring section recited in the claims corresponds to the refractivity measuring section 20.

Next, a first operational example of the visual training device 1 shown in FIG. 1 will be described with reference to FIGS. 2 and 3.

Figure 2:
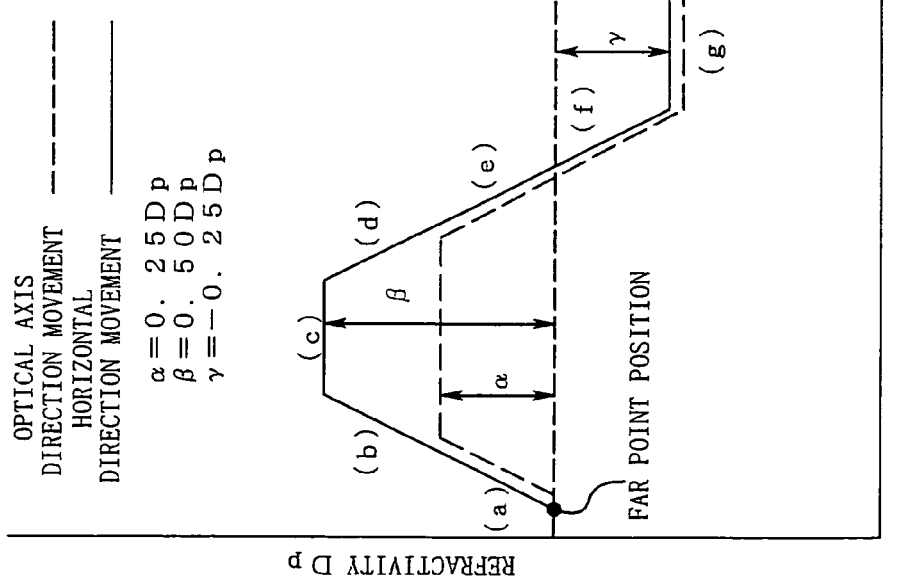
FIG. 2 is an explanatory diagram showing a state where a target moves in an optical axis direction as well as in a horizontal direction in the visual training device shown in FIG. 1 by using refractivity (Dp) (a first explanatory diagram showing an operation)

FIG. 2 is an explanatory diagram showing positions of a moving target (the target 11a moves in the optical axis direction as well as in the horizontal direction) by using refractivity (diopter) Dp. The abscissa axis indicates time, and the ordinate axis indicates the position of the target 11a represented in refractivity Dp. In FIG. 2, a solid line indicates the horizontal movement of the target while a dot line indicates the movement of the target in the optical axis direction.

Figure 3:
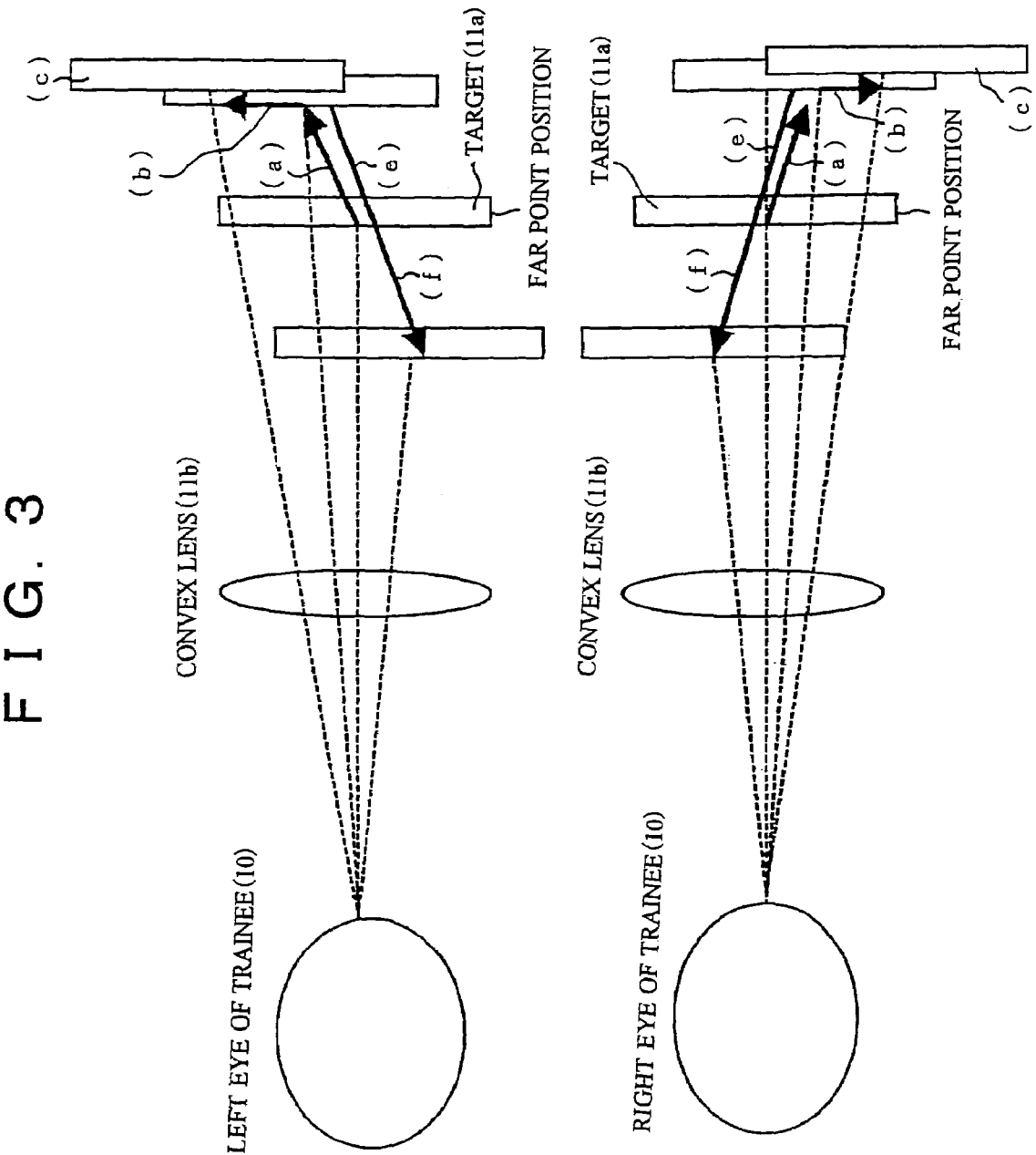
FIG. 3 is an explanatory diagram showing a positional change of the targets and a change in convergence angle when the targets move as shown in FIG. 2.

FIG. 3 is an explanatory diagram showing positional changes of the targets 11a and a change in convergence angle when the targets 11a move as shown in FIG. 2. In FIG. 3, the movement of the targets 11a in the optical axis direction and the horizontal movement of the target 11a (a change in convergence angle) are schematically illustrated.

The reference symbols in parentheses in FIG. 2 such as (a), (b), etc. and the same reference symbols in FIG. 3 indicate the same movement of the target 11a.

At the start of training, the targets 11a are set at far points of the eyes of a trainee (see a black spot in FIG. 2) by the optical axial movement section 11c based on the measurement information of the eyes measured by the refractivity measuring section 20. Moreover, a pair of the targets 11a are set at positions by the horizontal movement section 11d such that the visual axes of the right and left eyes of the trainee 10 become parallel. Specifically, the right and left targets 11a are set to have a papillary distance therebetween.

Next, as shown with the reference symbol (a) in FIGS. 2 and 3, the optical axial movement section 11c and the horizontal movement section 11d moves the targets 11a simultaneously in the optical axis direction and the horizontal direction to a position, the far point +α (in this case, α is +0.25 Dp) according to the measurement information of the eyes of a trainee 10 measured by the refractivity measuring section 20.

Next, as shown with the reference symbol (b) in FIGS. 2 and 3, the targets 11a keep moving only in the horizontal direction and stops moving in the optical axis direction by the function of the horizontal movement section 11d according to the measurement information of the eyes of a trainee 10 measured by the refractivity measuring section 20. As illustrated, +β is +0.5 Dp corresponding to the amount of movement in this case. As a result, the targets 11a move only horizontally to the position of +0.5 Dp while the positions thereof in the optical axis direction remain at +0.25 Dp.

The above-described point α=+0.25 Dp in the optical axis direction is set because of the following reasons. Specifically, if the targets 11a are moved too far from the far point, an image of the target is blurred. Moreover, some people cannot perceive that the image blurs because it locates at a far position. Therefore, with the above-described value the target 11 is positioned so that its image blurs little (where a blur is not perceivable).

From the above point α=+0.25 Dp, the targets 11a move only in the horizontal direction (convergence) so that the visual lines of the eyes of a trainee 10 incline outward toward the end in the horizontal direction at a point which is far beyond the far point therefore, the trainee does not perceive blur.

Generally, it is known that the convergence and the accommodation of eyes occur in synchronization with each other. Therefore, as the visual axes separate from each other, the accommodation of eyes is eased.

In this embodiment, convergence occurs to such an extent that the visual lines of the eyes separate from each other to incline outward toward the end, which does not occur in normal circumstances and stimulates the eyes. Therefore, eyestrain can be more eased than usual. This makes it possible to obtain the effects of easing eyestrain and increase the speed of easing.

Figure 8:
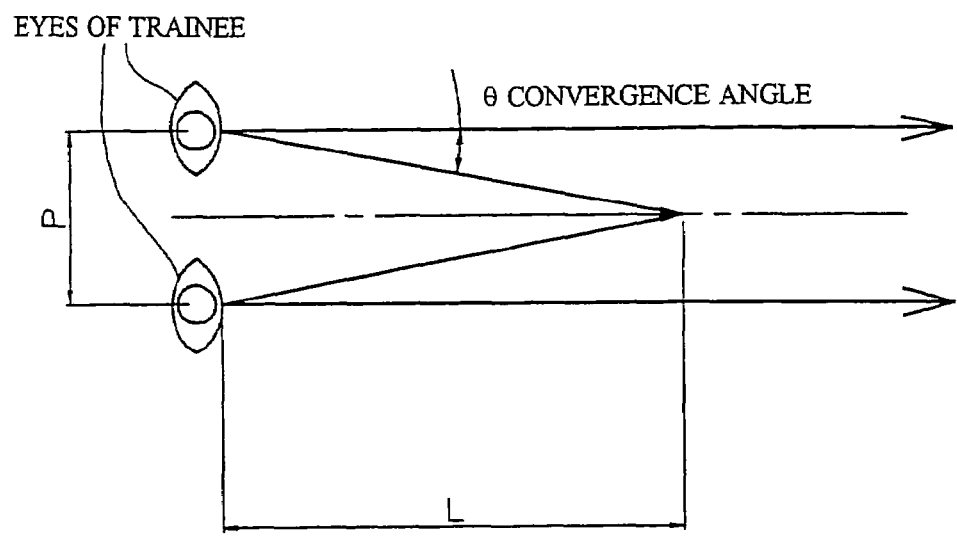
FIG. 8 is an explanatory diagram showing a convergence angle when a human views an object at a varying distance with his/her both eyes.

Note that the positional relation between the convergence angle θ and the target 11a is determined so as to establish the above-described formulae (1) and (2). In the case where the visual axes move further to incline outward on the far side, it is considered that the visual axes moves in the opposite direction by the same value of Dp (see FIG. 8).

Next, as shown with (c) in FIG. 2, the targets 11a stop moving to remain immobile for several seconds. Subsequently, as shown with (d) in FIG. 2, the targets 11a move inward in the horizontal direction. Next, as shown with (e) in FIGS. 2 and 3, when the targets 11a reach the positions +α (+0.25 Dp), the targets 11a restart moving in the optical axis direction (moving closer to the far point) while keeping moving in the horizontal direction.

Subsequently, as shown with (f) in FIGS. 2 and 3, when the targets 11a pass the far points and reach positions +γ, the targets 11a are stopped by the optical axial movement section 11c and the horizontal movement section 11d. Herein, γ is a value of −0.25 Dp.

Next, as shown with (g) in FIG. 2, the targets 11a stop moving and remain immobile for several seconds. Then, as shown with (h) in FIG. 2, the targets 11a restart moving in the optical axis direction toward the far points while horizontally moving. Thereafter, the same movements as those shown with (a) to (h) described above are repeated.

At a line (i) in FIG. 2, if the refractivity (Dp) of the eye of the trainee 10, which is measured by the refractivity measuring section 20, shifts to the positive value side from the previously measured value (that is, if the eyestrain of the trainee is eased), the same movements are repeated with the targets shifting by the amount of change in diopter x only in the optical axis direction. Lines (j), (k) and (m) in FIG. 2 indicate the movements in such a case (see the amount +x in FIG. 2). If the refractivity (Dp) of the eye of the trainee 10, which is measured by the refractivity measuring section 20, remains unchanged, the same movements as the precedent movements are repeated.

A predetermined number of sets (for example, five sets) of the above-described movements are repeated or the above-described movements are repeated for a predetermined amount of time (for example, one minute), and the training completes.

A second operational example of the visual training device 1 shown in FIG. 1 will now be described with reference to FIG. 4.

Figure 4:
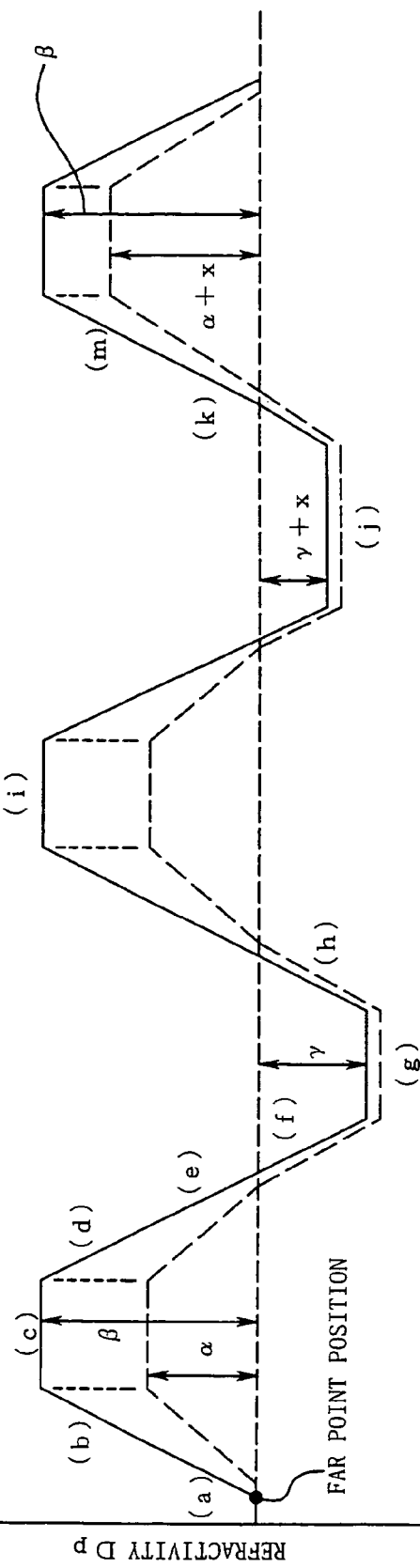
FIG. 4 is an explanatory diagram showing a state where the target moves in the optical axis direction as well as in the horizontal direction in the visual training device showing in FIG. 1 by using refractivity (Dp) (a second explanatory diagram showing an operation)

The operational example shown in FIG. 4 is as follows. Specifically, as shown with (a) and (b) in FIG. 4, the targets 11a move in the optical axis direction to the positions +α (in this case, α is +0.25 Dp) from the far points and in the horizontal direction to the positions +β (in this case, β is +0.50 Dp) at the same timing.

Similarly, as shown with (d) and (e) in FIG. 4, the targets 11a move in the optical axial direction to the far point (+α to 0) and move in the horizontal direction (+β to 0) at the same timing.

In the first operational example, the positional relation between the convergence angle and the targets is determined so as to establish the formulae (1) and (2). The positional relation between the divergence, in which the visual axes move away from each other in the horizontal direction on the far side, and the targets is also determined to establish the formulae (1) and (2). In the second operational example shown in FIG. 4, however, the targets 11a as shown with (a) and (b), and (d) and (e) move in the optical axis direction as well as in the horizontal direction (convergence or divergence) at the same timing. More specifically, the targets 11a move in the horizontal direction (convergence or divergence) to the positions corresponding to +0.5 Dp, while they move in the optical axis direction to the positions corresponding to +0.25 Dp (shown with vertical dot lines in FIG. 4). Therefore, the targets 11a are controlled to move at a ratio different from that in the first operational example, in other words, the formulae (1) and (2) are not established. The eyes of the trainee are accommodated in accordance with the movement of the targets 11a. Note that At (c) in FIG. 4, the targets 11a are stopped for several seconds as in the first operational example.

At (f) and (h) in FIG. 4, the targets 11a move in the horizontal direction (convergence) and in the optical axis direction in synchronization in a way that the formulae (1) and (2) is established. The eyes of the trainee are accommodated in accordance with the movements of the targets 11a. These movements are the same as those of the first operational example shown in FIG. 2. Thereafter, the same movements as those described above are repeated.

At (i) in FIG. 4, if the refractivity (Dp) of the eye of the trainee 10, which is measured by the refractivity measuring section 20, shifts toward the positive value side from the previously measured value (that is, if the eyestrain of the trainee is eased), the same movements are repeated with the targets shifting by the amount of change in diopter x only in the optical axis direction. Lines (j), (k) and (m) in FIG. 4 indicate the movements in such a case (see the amount +x in FIG. 4).

If the refractivity (Dp) of the eye of the trainee 10, which is measured by the refractivity measuring section 20, remains unchanged, the same movements as the precedent movements are repeated.

A predetermined number of sets (for example, five sets) of the above-described movements are repeated or the above-described movements are repeated for a predetermined amount of time (for example, a minute), and the training completes.

In the first operational example shown in FIG. 2 and the second operational example shown in FIG. 4, the movement of the targets 11a in the optical axis direction from the far points and in the horizontal direction are separately controlled. However, the present invention is not limited thereto. The positions at which the visual axes of right and left eyes incline outward toward the ends may be any positions as long as they are in the proximity of the far points on the optical axes. Herein, although varying depending on the state of eyes of a trainee, the proximity of the far point is preferably within the range of −0.25 Dp to +0.25 Dp further from the far point as the center. Similarly, the positional limit of the movement in the optical axis direction is defined as the position +0.25 Dp further from the far point in the above-described first and second examples of operation. However, although varying depending on the state of eyes of a trainee, the positional limit is preferably provided at the position corresponding to +0.15 to +0.35 Dp further from the far point. However, the positional limit will never be before the proximity of the far point on the optical axis described above (side of the eye of the trainee).

Figure 5:
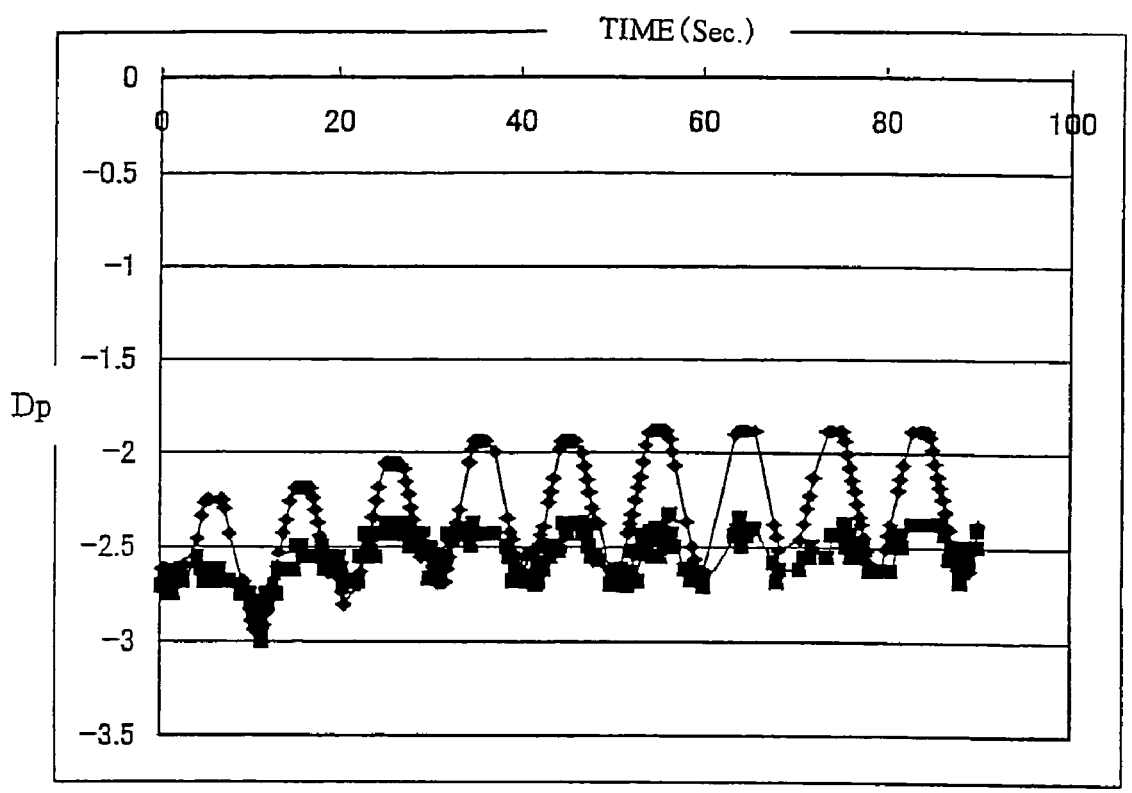
FIG. 5 shows the measurement results of refractivity (Dp) of the eyes of a test subject by using the visual training device shown in FIG. 1.

FIG. 5 shows an example of the measurement results of the refractivity (Dp) of the eye of the trainee 10, which is displayed on the display section 22 shown in FIG. 1. In FIG. 5, the abscissa axis indicates time while the ordinate axis indicates the refractivity (Dp). In FIG. 5, measurement marks represented in rhombic shape indicate the movement of the target 11a while measurement marks represented in rectangular shape indicate the measurement results of the refractivity (Dp) of the trainee.

As described in the first and second examples of operation, it can be seen from the drawing that the graph lines generally go upwards from left to right and the far points gradually shift to the positive value side as the targets 11a repeatedly make the defined movements. This signifies that the eyestrain of the trainee 10 is gradually relaxed and his eye fatigue is relieved.

The target 11a also moves, shifting to the positive value side, and moves repeatedly as the far point shifts toward the positive value side. It is possible to check up the training results of the trainee by just viewing the display section 22 in FIG. 1 which displays continuous measurement results in accordance with the movements of the targets 11a.

Next, the effects of the embodiment according to the present invention will be specifically described with reference to FIGS. 6 and 7.

FIG. 6 shows the results of training the eyes in a conventional method in which targets are repeatedly moved from near to far in the optical axes of right and left eyes.

FIG. 7 shows the results of visual training according to the embodiment of the present invention; that is, targets are repeatedly moved from near to far in the optical axes of right and left eyes while being moved until the visual lines thereof incline outward. In FIGS. 6 and 7, the number of test subjects is twelve (in the drawings, denoted as sub. 1 to sub. 12).

Before the experiments, the relaxation time for which the eyes of each of the twelve test subjects are relaxed is measured. The relaxation time corresponds to time taken for the eye muscles to recover from a strained state. The relaxation time is shown in the column "normal (A)" in FIGS. 6 and 7. In comparing the relaxation time when the eyes get fatigued with that when the eyes are not fatigued, the former is longer than the latter.

Next, each of the subjects views three-dimensional images for 30 minutes so as to fatigue the eyes. Then, after they are trained by the above-described conventional method, the relaxation time of the eyes is measured again. In FIG. 6, the relaxation time is shown in the column "after training (B)". Then, a difference in relaxation time between the normal state and after training is calculated. In FIG. 6, the time difference is shown in the column "(B)–(A)".

Similarly, each of the subjects keeps viewing three-dimensional images for 30 minutes so as to fatigue the eyes. Then, after they are trained by the above-described method according to the embodiment of the present invention, the relaxation time of the eyes is measured again. In FIG. 7, the relaxation time is shown in the column "after training (B)" as in FIG. 6. Then, a difference in relaxation time between the normal state and after training is calculated. In FIG. 7, the time difference is shown in the column "(B)–(A)" as in FIG. 6.

If a value of "(B)–(A)" is 0 or a negative value, the eyes restores its normal state, or the relaxation time of the eyes is shorter than in the normal state. This result shows that the training is effective.

On the other hand, in a case where a value of "(B)–(A)" is a positive value, the relaxation time after the training is longer than that when the eyes are not fatigued. This means that eyestrain persists even after the training, and the effectiveness of the training is low. Accordingly, the effectiveness of the visual training is apparent from the values of "(B)–(A)" in FIGS. 6 and 7.

Next, with reference to FIGS. 6 and 7, the values of "(B)–(A)" of the twelve subjects will be examined. In the case of applying the conventional method shown in FIG. 6, three out of the twelve subjects (25%) have a negative value in time difference "(B)–(A)". On the contrary, in applying the method according to the embodiment of the present invention shown in FIG. 7, eight out of twelve subjects (67%) have 0 or a negative value in time difference "(B)–(A)".

Moreover, in comparing average values in "(B)–(A)" of the twelve subjects between the conventional method of FIG. 6 and the method according to the present invention of FIG. 7, the average value is about 0.87 in the former whereas it is about −0.0058 in the latter. These results confirm that the visual training method according to the embodiment of the present invention is more effective than the conventional method.

Although the refractivity measuring section 20 (see FIG. 1) is provided in the above-described embodiment, the present invention is not limited thereto. Specifically, the control section 21, the optical axial movement section 11c and the horizontal movement section 11d can move the targets without the refractivity measuring section 20 as shown in FIGS. 2 to 4.

Moreover, although the target itself is vertically and horizontally moved in the above-described embodiment, the present invention is not limited thereto. The target may be moved vertically and horizontally by use of a mechanism for projecting an image serving as a target. Alternatively, a target may be displayed and moved on a small liquid crystal display. In such a case, the image may be preferably an attractive graphic mark (vertically and horizontally movable one such as airplane or car) which is perceivable by a trainee and appropriate to move horizontally around on the center of the screen where the trainee is likely to view).

Furthermore, the convex lens is used as an optical element for allowing a target to appear to be at a further position than it really is in the above-described embodiment, however;

need less to say that the other optical elements such as a hologram element can also be used.

The above-described embodiment employs a method of actually moving the target when moving an apparent position of the target on the optical axis, however, the present invention is not limited thereto. Any other methods such as a method of moving an optical system instead of the target can be used as long as the apparent position is movable.

Furthermore, the above embodiment has described a device to be used on a desk or the like. However, the present invention is not limited thereto. Any devices for projecting images onto the right eye and left eye (for example, a head mount display (HMD) and the like) can offer the same effects.

Furthermore, the above embodiment employs the device for moving the target 11a as shown in FIG. 1, however; the present invention is not limited thereto. The target 11a may be moved as shown in FIGS. 2 to 4, for example, on the screen of a computer. In this case, the present invention can be realized on the screen of a computer by use of software.

Moreover, in the above-described embodiment, the visual axes of the right and left eyes move in the optical axis directions as well as in the directions perpendicular to the optical axes, following the targets. However, the present invention is not limited thereto. Only either of the eyes may move in the optical axis direction as well as in the direction perpendicular to the optical axis direction, following the target.

Furthermore, the above-described embodiment employs two different mechanisms for separately moving the target in the optical axis direction and in the direction perpendicular to the optical axis direction (horizontal direction) (see the optical axial movement section 11a and the horizontal movement section 11d in FIG. 1). However, the present invention is not limited thereto. A single mechanism for diagonally moving the target may also be used instead.

The invention is not limited to the above embodiments and various modifications may be made without departing from the spirit and scope of the invention. Any improvement may be made in part or all of the components.

What is claimed is:

1. A visual training method, comprising:
a first step of displaying respective separate targets for right and left eyes of a trainee; and
a second step of moving positions of the separate targets displayed for the right and left eyes in directions of respective optical axes of the right and left eyes while simultaneously moving the positions in horizontal directions perpendicular to the optical axes of the right and left eyes until visual lines of the right and left eyes incline outward.

2. The method according to claim 1, wherein
in the second step the positions of the targets are moved further beyond far points in the optical axis directions while the positions of the targets are aligned with focal points of the right and left eyes.

3. The method according to claim 2, wherein
in the second step the targets are moved in the optical axis directions and in the horizontal directions perpendicular to the optical axes of the right and left eyes in parallel until the targets reach predefined positions in the optical axis directions, and thereafter the targets are moved only in the horizontal directions perpendicular to the optical axes.

4. The method according to claim 3, wherein
the visual lines of the right and left eyes are parallel to each other at the predefined positions in the optical axis directions.

5. The method according to claim 1, wherein
in the second step the targets are moved in the optical axis directions and in the horizontal directions perpendicular to the optical axes of the right and left eyes in parallel until the targets reach predefined positions in the optical axis directions, and thereafter the targets are moved only in the horizontal directions perpendicular to the optical axes.

6. The method according to claim 5, wherein
in the second step the positions in which the visual lines of the right and left eyes incline outward are in the proximity of far points on the optical axes of the right and left eyes.

7. The method according to claim 1, wherein
in the second step positions in which the visual lines of the right and left eyes incline outward are in the proximity of far points on the optical axes.

8. The method according to claim 7, wherein
the visual lines of the right and left eyes are parallel to each other at predefined positions in the optical axis directions.

9. The method according to claim 2, wherein
in the second step the positions in which the visual lines of the right and left eyes incline outward are in the proximity of far points on the optical axes of the right and left eyes.

10. The method according to claim 5, wherein
the predefined positions in the optical axis directions are in the proximity of a position +0.25 Dp further from far points in the optical axis directions.

11. The method according to claim 5, wherein
the visual lines of the right and left eyes are parallel to each other at the predefined positions in the optical axis directions.

12. A visual training method comprising:
a first step of displaying respective separate targets for right and left eyes of a trainee;
a second step of moving positions of the separate targets displayed for the right and left eyes in directions of respective optical axes of the right and left eyes while simultaneously moving the positions in horizontal directions perpendicular to the respective optical axes of the right and left eyes until visual lines of the right and left eyes incline outward;
a third step of measuring refractivities of the right and left eyes;
a fourth step of determining positions to which the separate targets are moved in the optical axis directions, according to results of the measurement in the third step; and
a fifth step of returning to the second step to move the separate targets to the positions determined in the fourth step and thereafter executing the third and fourth steps again.

13. A visual training device comprising:
a target display section for displaying respective separate targets for right and left eyes of a trainee;
an optical axial movement section for moving positions of the separate targets displayed for the right and left eyes in directions of respective optical axes of the right and left eyes; and
a horizontal movement section for moving the separate targets displayed for the right and left eyes in horizontal directions perpendicular to the optical axes of the right and left eyes until visual lines of the right and left eyes incline outward.

14. The device according to claim 13, wherein the target display section is a means for projecting an image serving as a target.

15. A visual training device comprising:

a target display section for displaying respective separate targets for right and left eyes of a trainee;

a refractivity measuring section for measuring refractivities of the right and left eyes;

an optical axis moving section for moving positions of the separate targets displayed for the right and left eyes in directions of respective optical axes of the right and left eyes, according to the refractivities of the right and left eyes measured by the refractivity measuring section; and a horizontal movement section for moving the separate targets displayed for the right and left eyes in horizontal directions perpendicular to the optical axes of the right and left eyes according to the refractivities of the right and left eyes measured by the refractivity measuring section until visual lines of the right and left eyes incline outward.

16. The device according to claim 15, wherein the target display section is a means for projecting an image serving as a target.

17. The device according to claim 15, further comprising a display section for simultaneously displaying a positional change of the targets caused by the horizontal direction moving section and the refractivities of the eyes of the trainee measured by the refractivity measuring section.

* * * * *